(12) United States Patent
Hernandez

(10) Patent No.: US 11,684,468 B2
(45) Date of Patent: Jun. 27, 2023

(54) SURGICAL CONSTRUCT WITH ADJUSTABLE LOOPS AND SLIDING KNOT

(71) Applicant: Arthrex, Inc., Naples, FL (US)

(72) Inventor: Luis A. Hernandez, Naples, FL (US)

(73) Assignee: Arthrex, Inc., Naples, FL (US)

( * ) Notice: Subject to any disclaimer, the term of this patent is extended or adjusted under 35 U.S.C. 154(b) by 735 days.

(21) Appl. No.: 16/674,814

(22) Filed: Nov. 5, 2019

(65) Prior Publication Data

US 2020/0138562 A1   May 7, 2020

Related U.S. Application Data

(60) Provisional application No. 62/756,253, filed on Nov. 6, 2018.

(51) Int. Cl.
*A61F 2/08* (2006.01)
*A61B 17/04* (2006.01)

(52) U.S. Cl.
CPC ..... *A61F 2/0811* (2013.01); *A61B 2017/0404* (2013.01); *A61F 2002/0852* (2013.01); *A61F 2002/0882* (2013.01)

(58) Field of Classification Search
CPC ............ A61F 2/0811; A61F 2002/0852; A61F 2002/0882; A61F 2/08; A61F 2250/0012; A61B 2017/0404; A61B 2017/0417; A61B 2017/0475; A61B 2017/0477
See application file for complete search history.

(56) References Cited

U.S. PATENT DOCUMENTS

| | | | |
|---|---|---|---|
| 5,222,978 A * | 6/1993 | Kaplan | A61L 17/005 606/228 |
| 5,645,588 A | 7/1997 | Graf et al. | |
| 5,769,894 A | 6/1998 | Ferragamo | |
| 6,517,578 B2 | 2/2003 | Hein | |
| 6,596,015 B1 * | 7/2003 | Pitt | A61B 17/0469 606/232 |
| 7,530,900 B2 | 5/2009 | Holt et al. | |
| 8,439,976 B2 | 5/2013 | Albertorio et al. | |
| 8,460,379 B2 | 6/2013 | Albertorio et al. | |
| 8,696,704 B2 * | 4/2014 | Selvitelli | A61B 17/0401 606/232 |
| 9,005,245 B2 | 4/2015 | Thornes et al. | |
| 9,463,008 B2 * | 10/2016 | Thal | A61B 17/0401 |
| 9,463,013 B2 | 10/2016 | Pilgeram et al. | |
| 9,561,027 B2 | 2/2017 | Perriello et al. | |
| 9,963,319 B2 | 5/2018 | Ferguson et al. | |
| 10,052,094 B2 * | 8/2018 | Spenciner | A61F 2/0811 |
| 10,881,500 B2 * | 1/2021 | Brunsvold | A61B 17/0401 |
| 11,039,830 B2 * | 6/2021 | Piccirillo | A61B 17/06166 |
| 11,219,519 B2 * | 1/2022 | Kam | A61B 17/0401 |
| 11,324,584 B2 * | 5/2022 | Brunsvold | A61B 17/8869 |
| 2015/0196385 A1 * | 7/2015 | Kam | A61B 17/0401 623/13.14 |
| 2016/0157851 A1 * | 6/2016 | Spenciner | A61F 2/0811 606/232 |
| 2017/0296328 A1 * | 10/2017 | Albertorio | A61F 2/0811 |

(Continued)

FOREIGN PATENT DOCUMENTS

WO   WO-2022024001 A1 *   2/2022   ......... A61B 17/0401

*Primary Examiner* — Suzette J Gherbi
(74) *Attorney, Agent, or Firm* — Blank Rome LLP

(57) ABSTRACT

This disclosure relates to methods of surgical tissue reconstruction, such as for joint or ligament repair, and associated surgical constructs.

28 Claims, 15 Drawing Sheets

(56) References Cited

U.S. PATENT DOCUMENTS

| | | | |
|---|---|---|---|
| 2019/0038276 A1* | 2/2019 | Jackson | A61F 2/0811 |
| 2020/0138562 A1* | 5/2020 | Hernandez | A61F 2/0811 |
| 2021/0093312 A1* | 4/2021 | Hernandez | A61B 17/0485 |
| 2021/0093316 A1* | 4/2021 | Gustafson | A61B 17/0485 |
| 2022/0096073 A1* | 3/2022 | Jackson | A61B 17/0401 |
| 2022/0167967 A1* | 6/2022 | Gustafson | A61B 17/06166 |
| 2022/0229101 A1* | 7/2022 | Lavedas | H04B 5/0081 |
| 2022/0265266 A1* | 8/2022 | Anderson | A61B 17/0401 |
| 2022/0273289 A1* | 9/2022 | Anderson | A61B 17/0483 |

\* cited by examiner

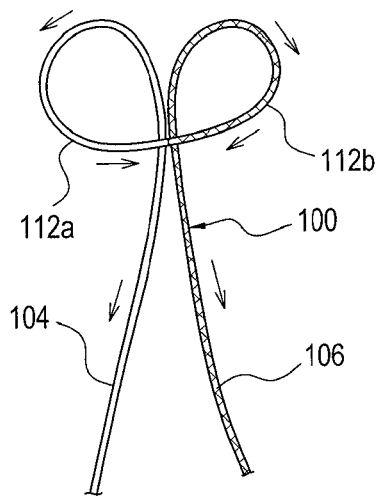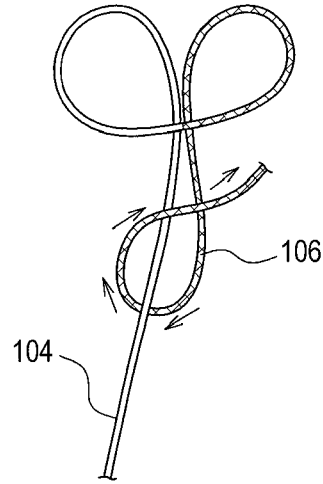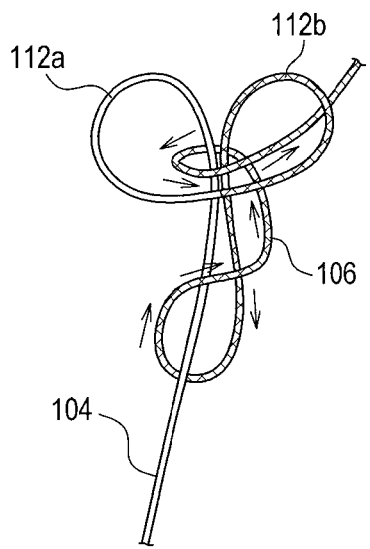
FIG. 2A  FIG. 2B  FIG. 2C
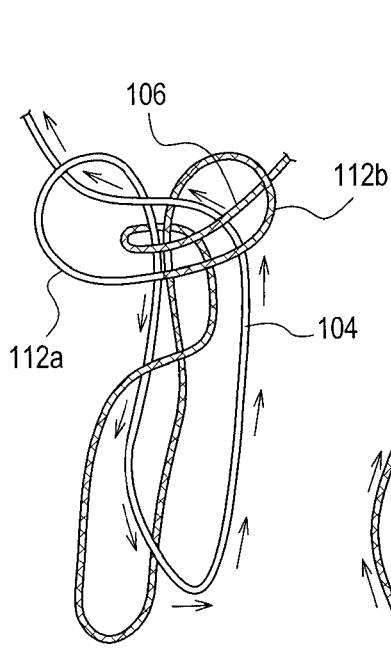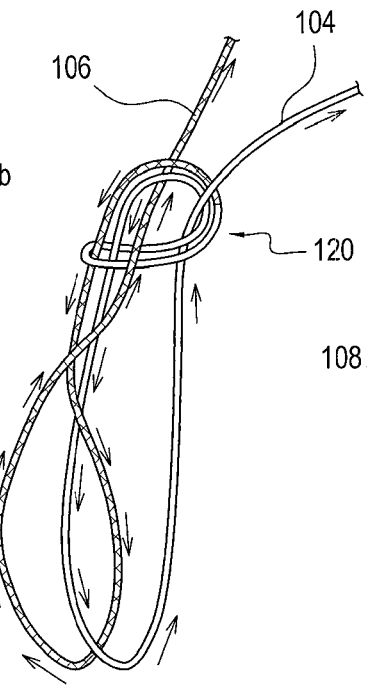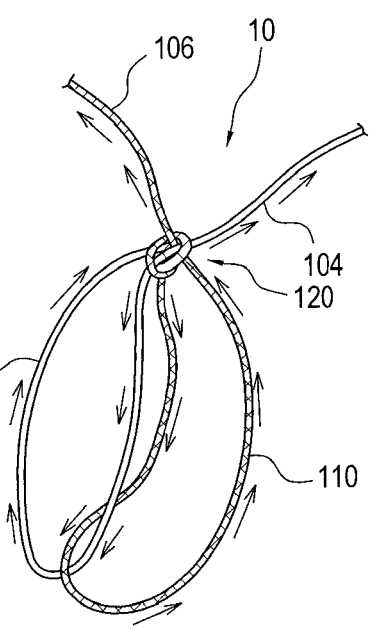
FIG. 2D  FIG. 2E  FIG. 2F

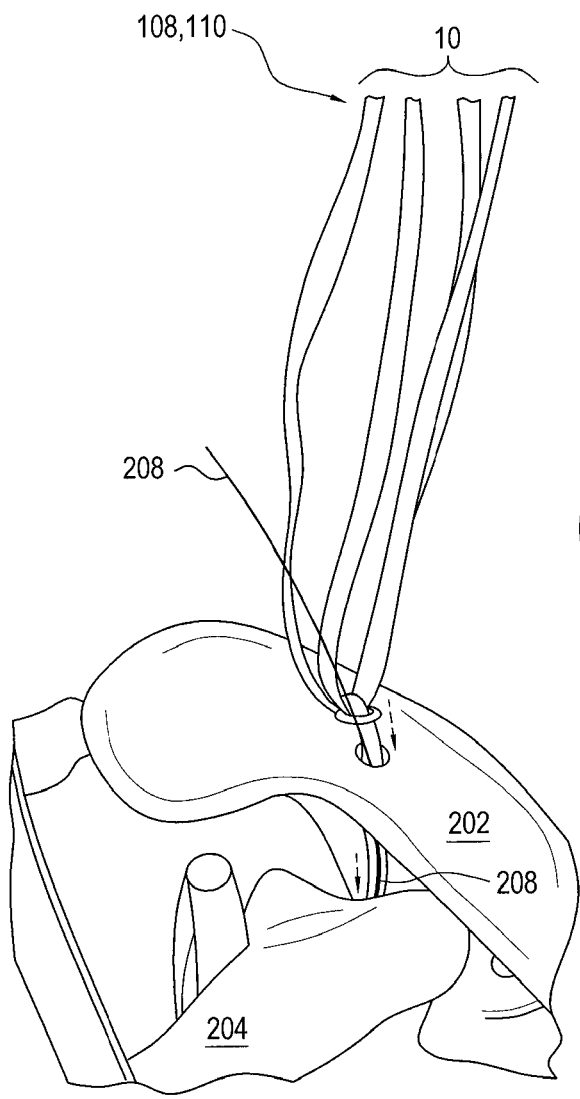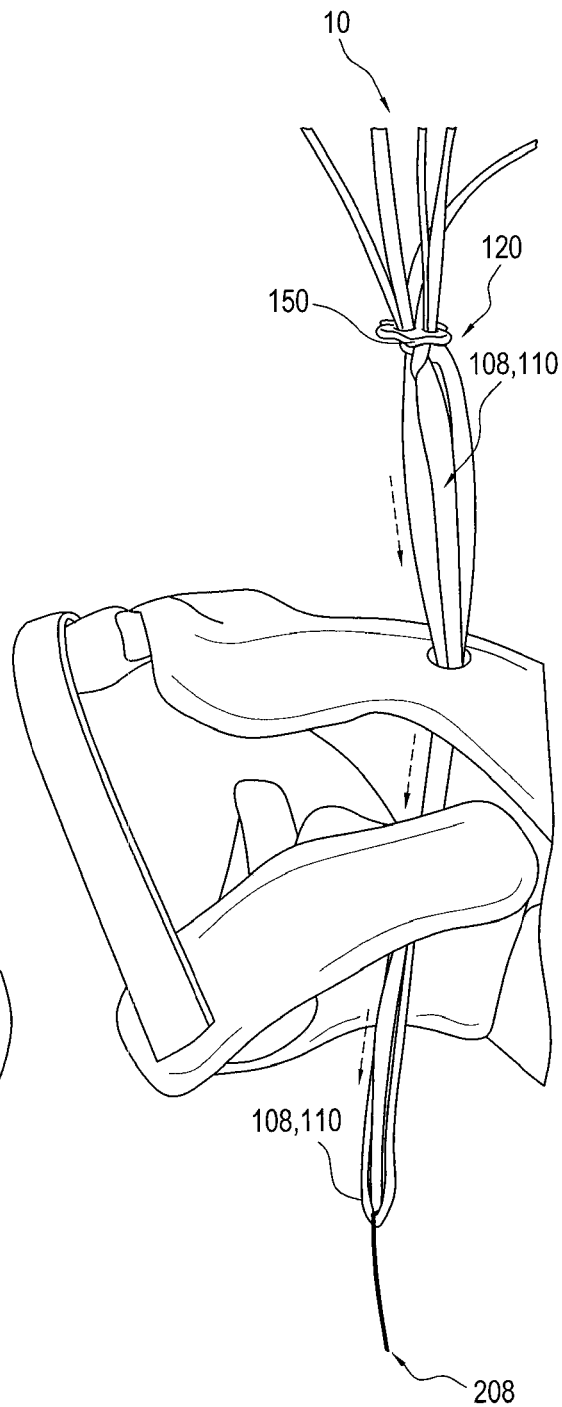
FIG. 6A
FIG. 6B

SURGICAL CONSTRUCT WITH ADJUSTABLE LOOPS AND SLIDING KNOT

RELATED APPLICATION

This application claims priority to Provisional Application No. 62/756,253, filed on Nov. 6, 2018, the entire disclosure of which is herein incorporated by reference.

BACKGROUND

This disclosure relates to surgical reconstruction, such as for joint or ligament repair, and associated surgical constructs.

Reconstructive surgeries, such as for the acromioclavicular joint (AC), the anterior cruciate ligament (ACL), or the CCL for canines, are well known. Methods of AC joint reconstruction are described, for example, in commonly owned U.S. Pat. No. 9,005,245, the subject matter of which is incorporated by reference. Improved reconstruction techniques are needed with easier adjustable loop fixation and a simplified construct that may be used for the reconstruction.

SUMMARY

This disclosure relates to a surgical construct that comprises a flexible strand that comprises a first segment, a second segment, and opposite first and second free ends corresponding to the first and second segments, respectively. The first segment forms a first adjustable loop and the second segment forms a second adjustable loop. Each of the first and second adjustable loops have a continuous loop portion and the continuous loop portions are interlocked with one another. A sliding knot couples the first and second segments. The sliding knot is configured to slidably receive the first and second free ends. The first and second adjustable loops are individually adjustable independent of one another by sliding the first and second free ends through the sliding knot.

The continuous loop portions of the first and second adjustable loops may be interconnected across from the sliding knot. The continuous loop portions may terminate at the sliding knot. The flexible strand is a single flexible strand. The flexible strand may be a suture or a suture tape. A fixation device may be coupled to the first and second free ends of the flexible strand. The fixation device may be located near the sliding knot. The fixation device may be a button that has apertures for receiving each of the first and second adjustable loops. The flexible strand is devoid of splicing.

This disclosure relates to a surgical construct for tissue reconstruction that comprises a single suture tape that comprises a first segment, a second segment, and opposite first and second free ends corresponding to the first and second segments, respectively. The first segment forms a first adjustable loop and the second segment forms a second adjustable loop. Each of the first and second adjustable loops has a continuous loop portion. A sliding knot couples the first and second segments and terminates the continuous loop portions. The sliding knot is configured to slidably receive the first and second free ends. The first and second adjustable loops are individually adjustable independent of one another by sliding the first and second free ends through the sliding knot.

A method of tissue reconstruction includes, inter alia, advancing a surgical construct in a first direction through first and second tissues, the surgical construct being formed of a flexible strand comprising first and second interlocked adjustable loops, a sliding knot, and first and second free ends slidable through the sliding knot; pulling the surgical construct in a second direction opposite the first direction at the first and second free ends thereof such that a fixation device coupled to the first and second adjustable loops engages the first tissue and closing a separation between the first and second tissues; and tensioning the surgical construct by pulling on the free ends to reduce the first and second adjustable loops and secure the first and second tissues together.

A method may include a step of engaging another fixation device coupled to free ends of a surgical construct with a second tissue, wherein tensioning the surgical construct by pulling on the free ends to reduce first and second adjustable loops, secures the first and second tissues together between fixation devices. This fixation device may be coupled to the free ends of the surgical construct prior to inserting the surgical construct through first and second bones. Each of the fixation devices may be a button.

In a method, the first and second adjustable loops may be individually adjustable by pulling the first and second free ends, respectively, when tensioning the surgical construct. First and second adjustable loops may be simultaneously adjustable by pulling on first and second free ends at the same time. First and second tissues may be first and second bones of a separated bone joint. Corresponding holes may be drilled into first and second bones and a surgical construct is advanced through the holes of the first and second bones. A sliding knot of a surgical construct may be placed in the hole of the second bone. When a surgical construct is advanced through first and second bones, adjustable loops of the surgical construct may be first inserted into holes of first and second bones, respectively. A fixation device may be coupled to adjustable loops of a surgical construct after advancing the surgical construct through the first and second bones.

BRIEF DESCRIPTION OF THE DRAWINGS

FIGS. 2A-2G illustrates steps for forming the surgical construct illustrated in FIGS. 1A and 1B.

FIGS. 6A-6L illustrate exemplary method steps for repairing a separated joint using the surgical construct illustrated in FIGS. 1A and 1B.

DETAILED DESCRIPTION

This disclosure generally relates to a surgical construct 10 and methods of tissue reconstruction using the same. Surgical construct 10 is designed to simplify reconstructive surgery while also providing a secure repair. In an embodiment, surgical construct 10 comprises only a single suture tape 100 that forms two adjustable loops with a sliding knot and without any splices in the construct. For simplicity, the surgical construct 10 and methods of reconstruction using the surgical construct 10 will be described in the context of an AC joint and CCL reconstructions. Surgical construct 10, however, is not limited to such reconstructions, and may be used for any reconstruction and/or fixation, including bone repair, cartilage repair, soft tissue repair, and the like.

Figure 1A:
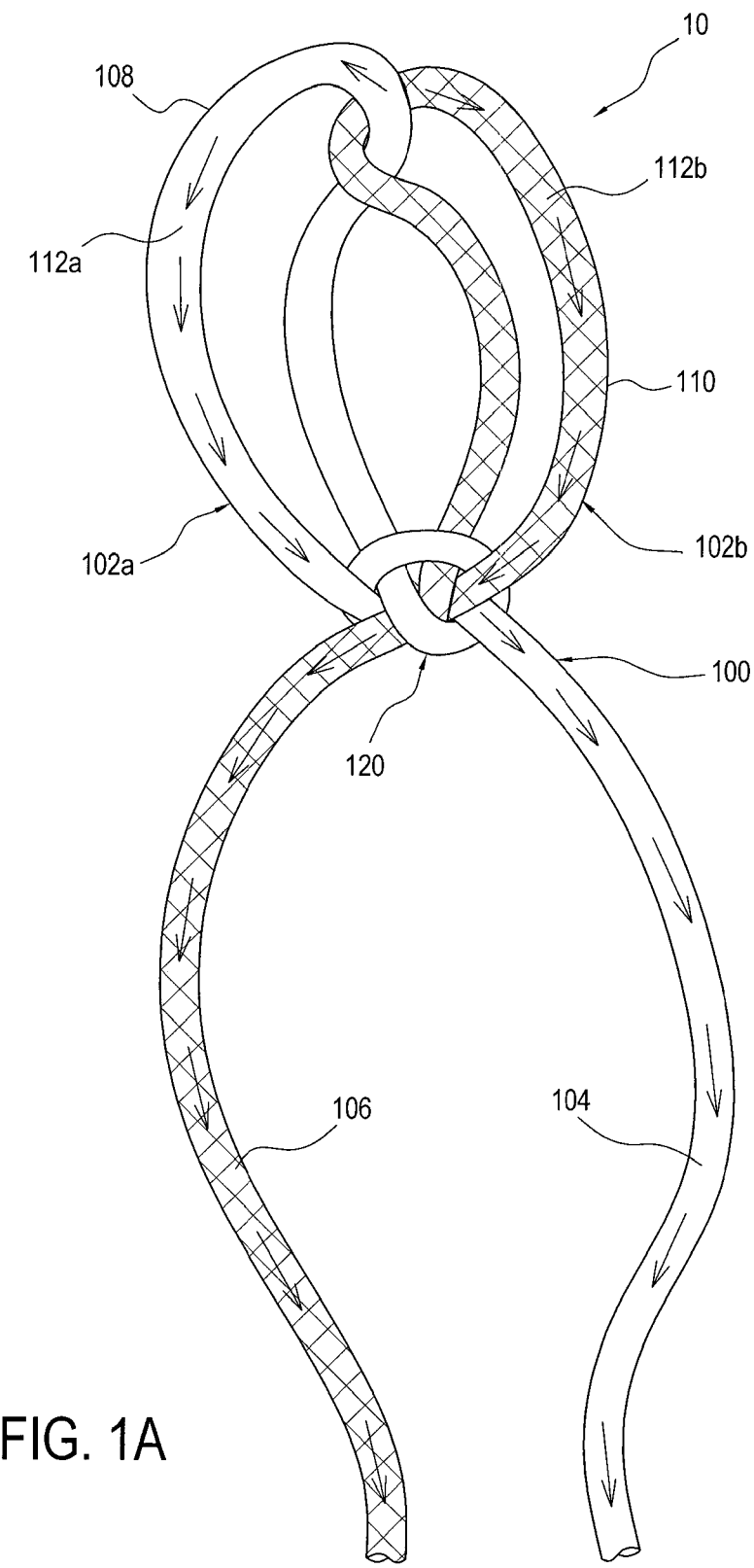
FIGS. 1A and 1B are opposite side views, respectively, of an exemplary surgical construct.
Figure 1B:
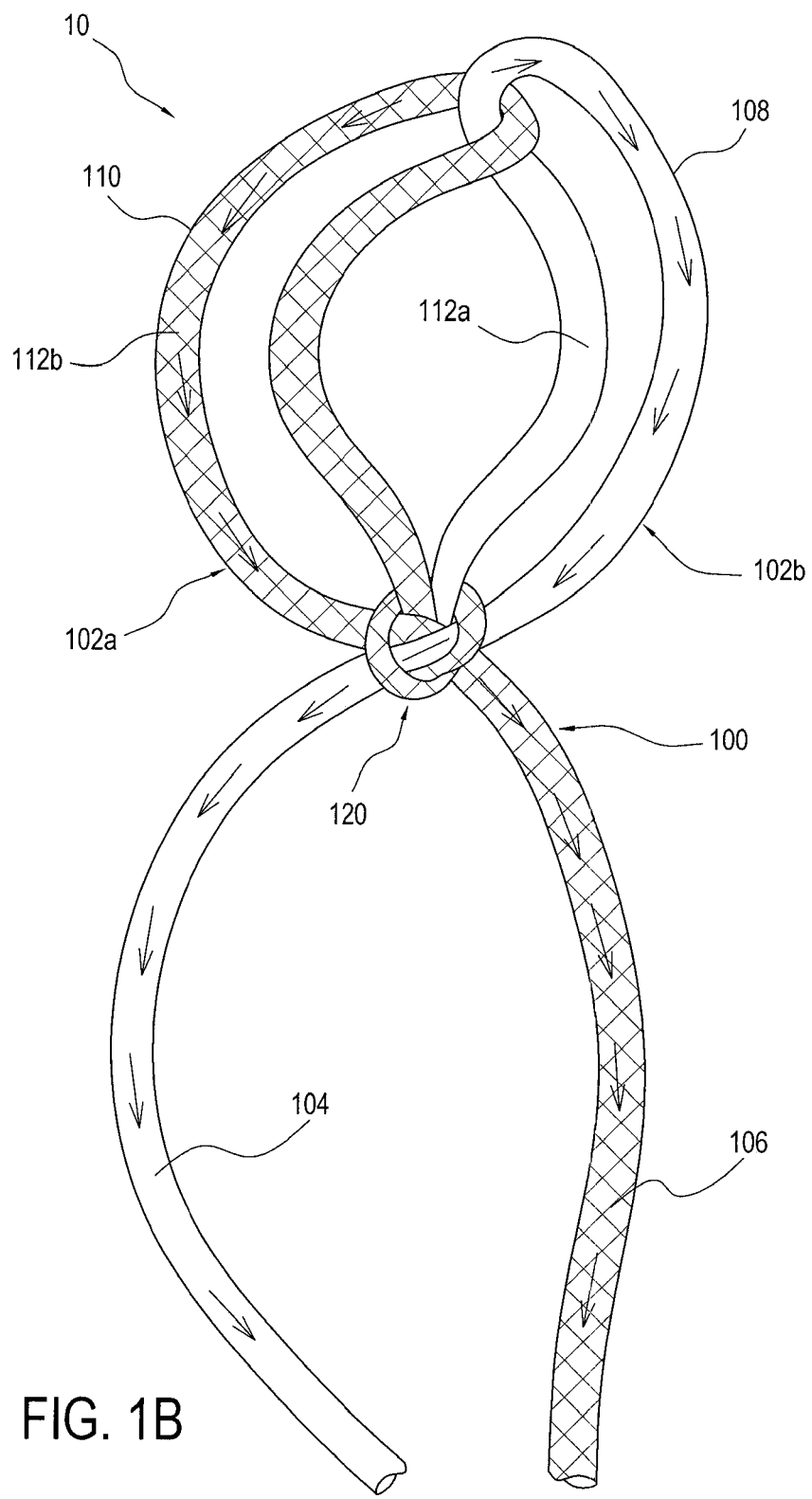

Referring to FIGS. 1A and 1B, surgical construct 10 generally includes a flexible strand 100 that comprises first and second segments 102a and 102b, and opposite first and second free ends 104 and 106 associated with the first and second segments 102a and 102b, respectively. First segment 102a forms a first adjustable loop 108 and second segment 102b forms a second adjustable loop 110. Each adjustable loop 108 and 110 has a continuous loop portion 112a and 112b. A sliding knot 120 is formed in flexible strand 100 which couples first and second adjustable loops 108 and 110. The continuous loop portions 112a and 112b may be interlocked with one another and the sliding knot 120 may terminate the continuous loop portions 112a and 112b across or opposite from where the loop portions are interlocked. The sliding knot 120 may be configured to slidably receive first and second free ends 104 and 106, with no or minimal friction, to allow individual adjustment of the adjustable loops 108 and 110 by pulling the first free end 104 and/or the second free end 106, either one at a time or at the same time.

Figure 2G:
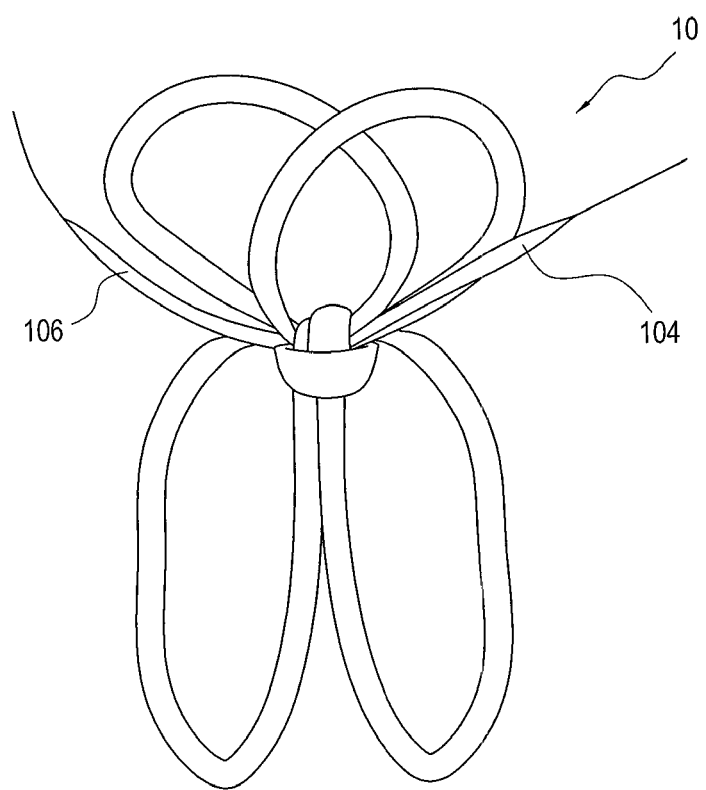

FIGS. 2A-2F illustrate an exemplary way of forming surgical construct 10. The surgical construct 10 may be formed using only a single flexible strand, such as a single suture or suture tape. Initially, the two continuous loop portions 112a and 112b are created in the first and second segments 102 and 102b of the flexible strand 100, as seen in FIG. 2A. Next, second free end 106 is crossed under and over first free end 104, as seen in FIG. 2B. Second free end 106 is then passed through and around continuous loop portion 112a and then through and out of continuous loop portion 112b, as seen in FIG. 2C. After that, first free end 104 is passed through and around continuous loop portion 112b and then through and out of continuous loop portion 112a, as seen in FIG. 2D. This builds two sliding loops. The free ends 104 and 106 are pulled to create the sliding knot 120, as seen in FIG. 2E. Finally, the sliding knot 120 may be closed to create the adjustable loops 108 and 110 and form construct 10, as seen in FIG. 2F, where the knot 120 allows free ends 104 and 106 to slide with respect to knot 120 to reduce or shrink the adjustable loops 108 and 110. The construct 10 is formed without the use of or the need for splicing the flexible strand. Thus, the construct 10 is devoid of splicing. FIG. 2G illustrates an additional step to create a strength lock on the knot 120 for the fixation, as an option for the surgeon. In this configuration of the free ends of the flexible strand on opposite directions will interlocked one on another through the sliding knot 120.

Figure 3A:
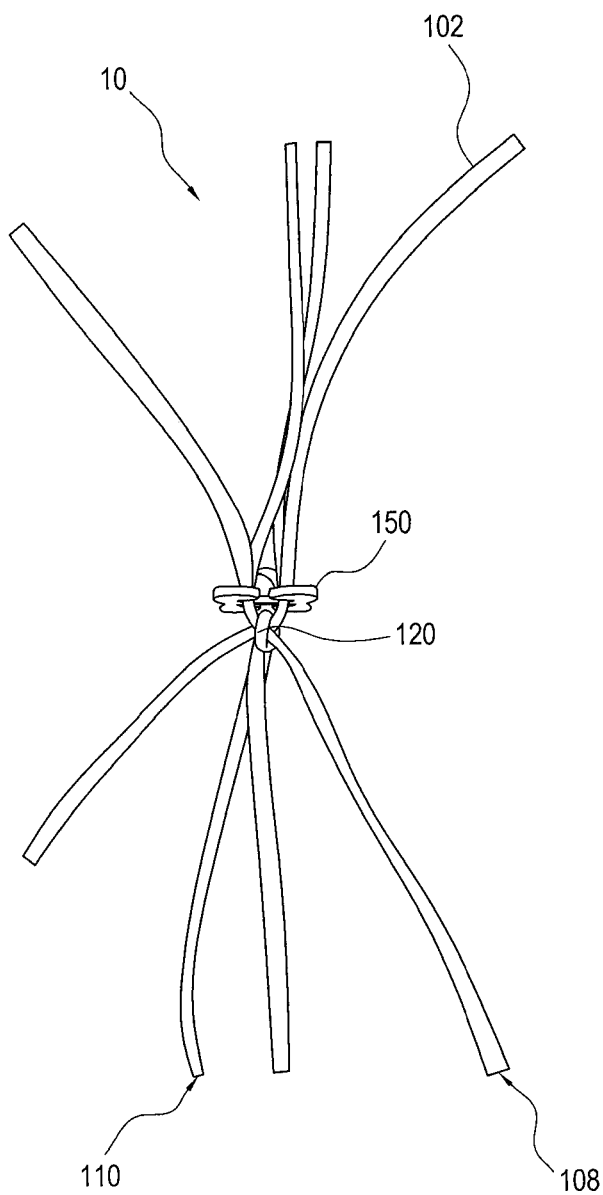
FIGS. 3A and 3B are opposite side views, respectively, of the surgical construct with a fixation device attached thereto.
Figure 3B:
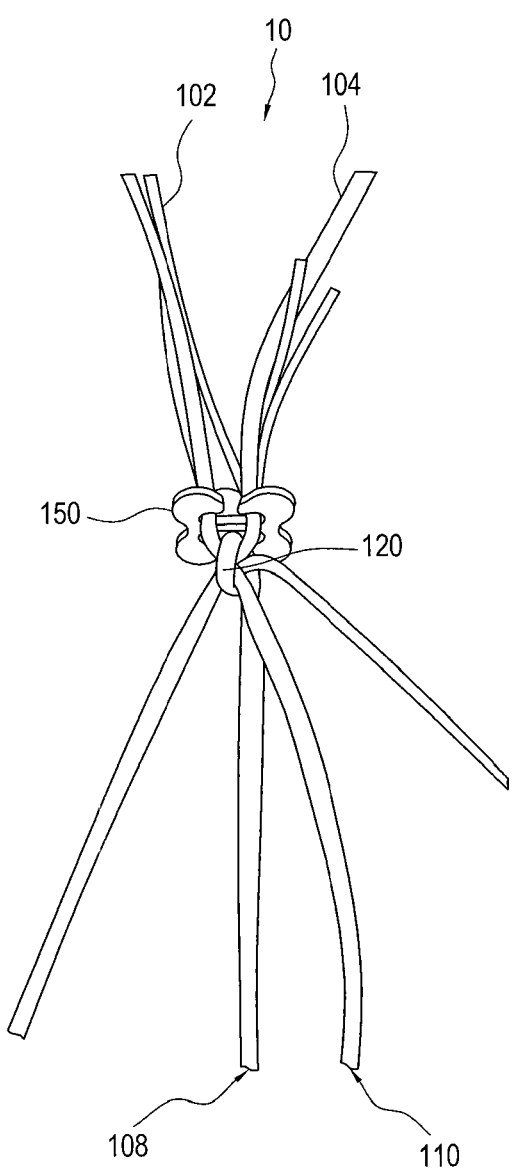

Surgical construct 10 may include a fixation device 150, as seen in FIGS. 3A and 3B. Fixation device 150 may be attached to surgical construct 10 at the side of sliding knot 120 of the free ends 104 and 106 of the construct 10. Fixation device 150, may be a button or the like, such as described in U.S. Pat. No. 9,005,245. The free ends 140 and 106 of construct 10 may extend through respective openings in the fixation device 150.

Figure 4:
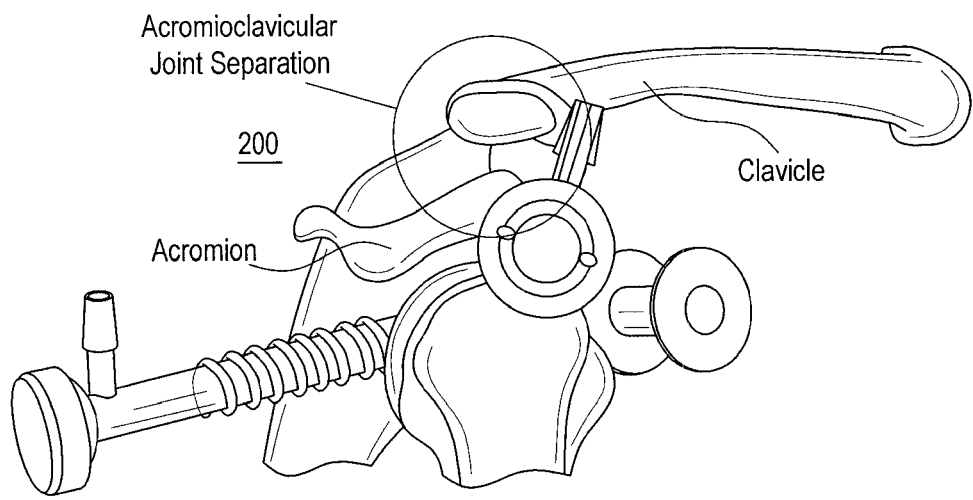
FIG. 4 is a perspective view of an exemplary joint separation needing reconstruction.
Figures 5A, 5B:
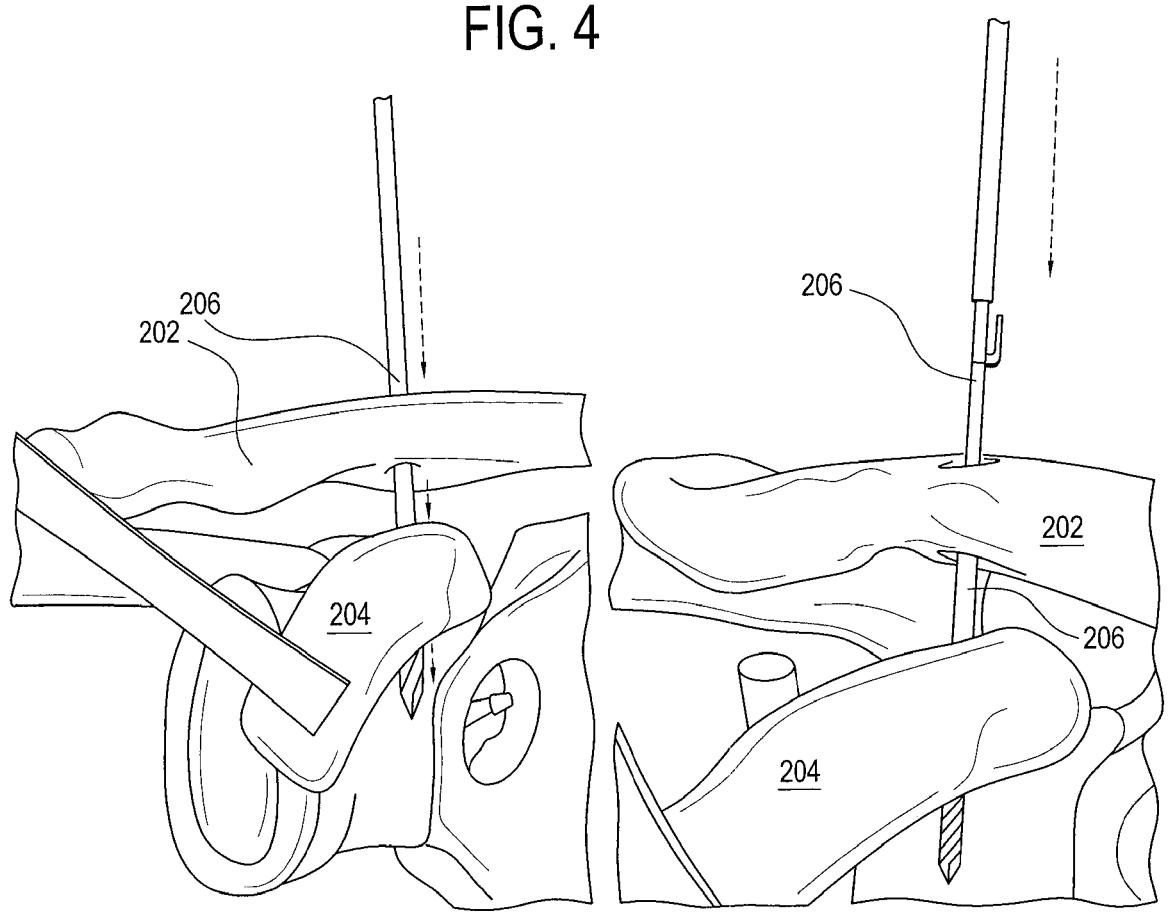
FIGS. 5A and 5B illustrate of the preparation steps of an exemplary method of joint reconstruction.

In an embodiment, surgical construct 10 may be used for tissue reconstruction, such as reconstruction of a separated joint 200, as seen in FIG. 4. The initial preparation steps of the reconstruction may include drilling corresponding holes in the separated bones, e.g. the clavicle and coracoid bone 202 and 204, using a cannulated drill 206, for example, as seen in FIGS. 5A and 5A, drilling from the clavicle 202 to the coracoid 204. With the cannulated drill 206 in place, a shuttling device 208 (FIGS. 6A and 6B), such as a Lasso wire, may be passed through the drill to facilitate advancement of the construct 10 through the bone holes. The drill may then be removed.

Next, as seen in FIGS. 6A and 6B, the shutting device 208 is coupled to the adjustable loops 108 and 110 of the surgical construct 10 to advance the construct in a first direction through the clavicle 202 to the coracoid 204, via the drilled holes thereof, with the adjustable loops 108 and 110 of the construct being inserted in the holes first and pulled through by the shuttling device. At this stage, the surgical construct 10 extends through both the clavicle 202 and the coracoid 204 and spans the separation therebetween, with the sliding knot 120 and the fixation device 150 at the superior side of the clavicle 202.

Figure 6C:
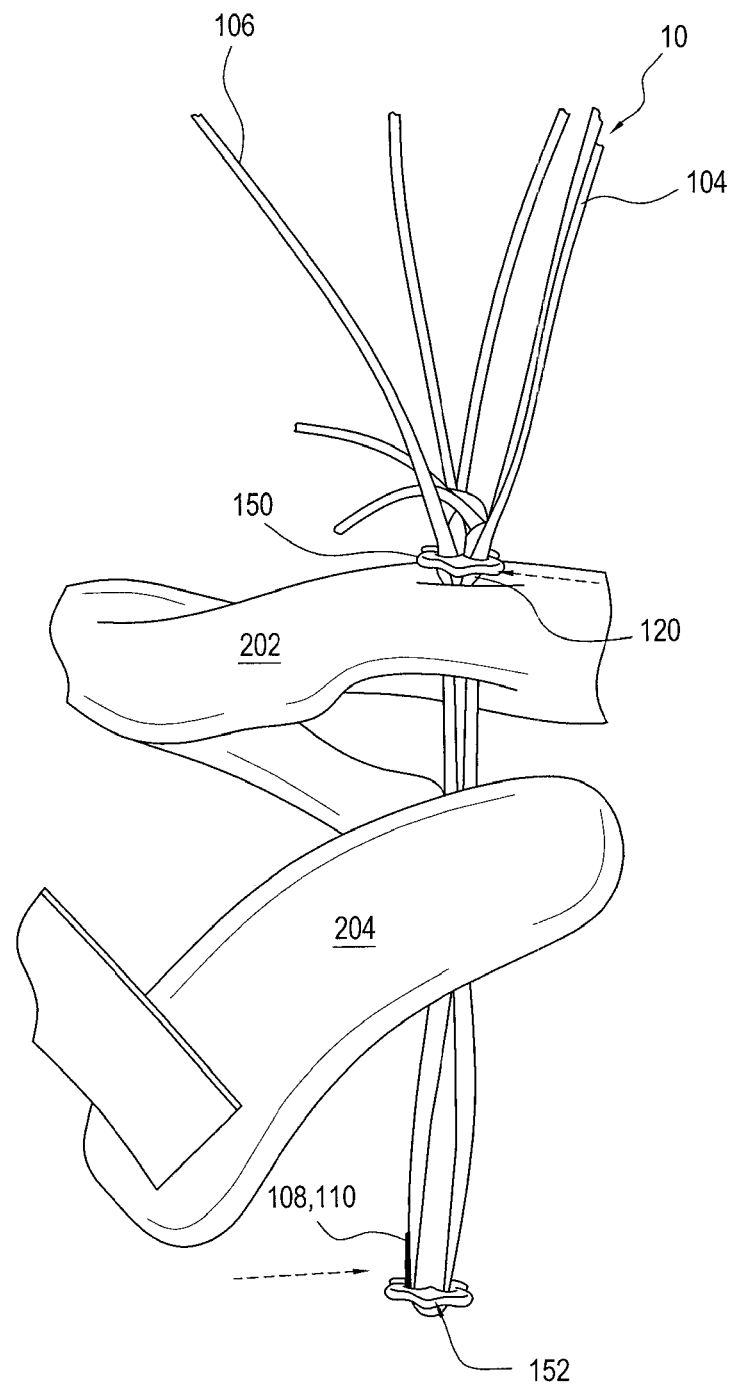
Figure 6D:
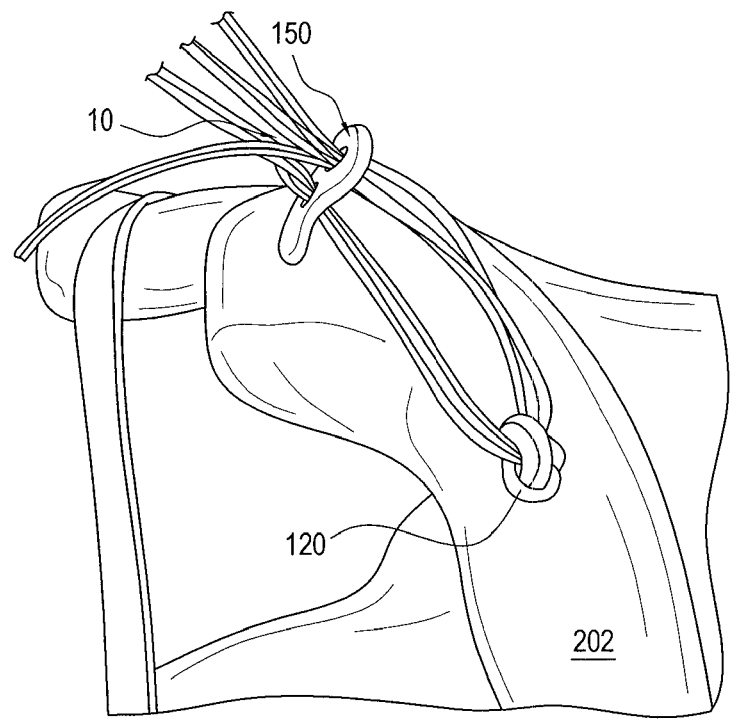

As seen in FIGS. 6C and 6D, the sliding knot 120 is then inserted into the drilled hole of the clavicle 202 by pulling on adjustable loops 108 and 110 at the superior side of the coracoid 204. Another fixation device 152 is attached to the adjustable loops 108 and 110. The fixation device 152 may be a button or the like that is attached to the flexible strand of the contrast 10 at loops 108 and 110 in a known manner.

Figure 6E:
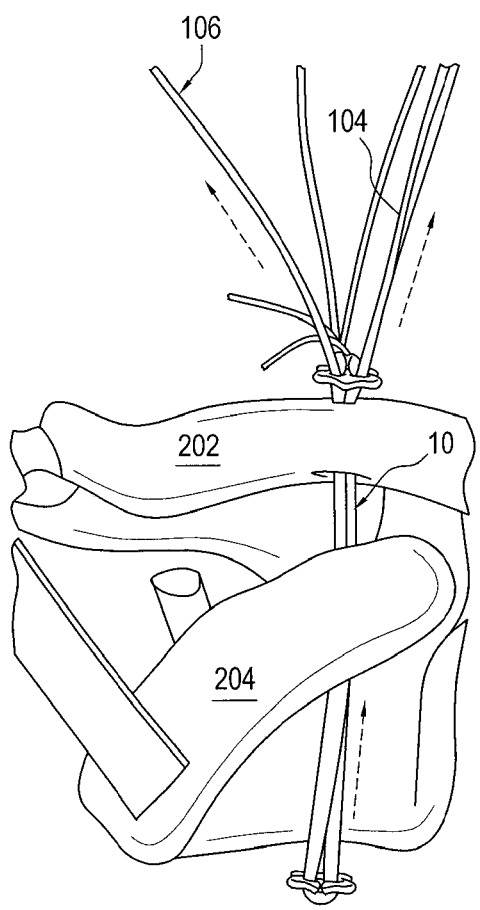
Figure 6F:
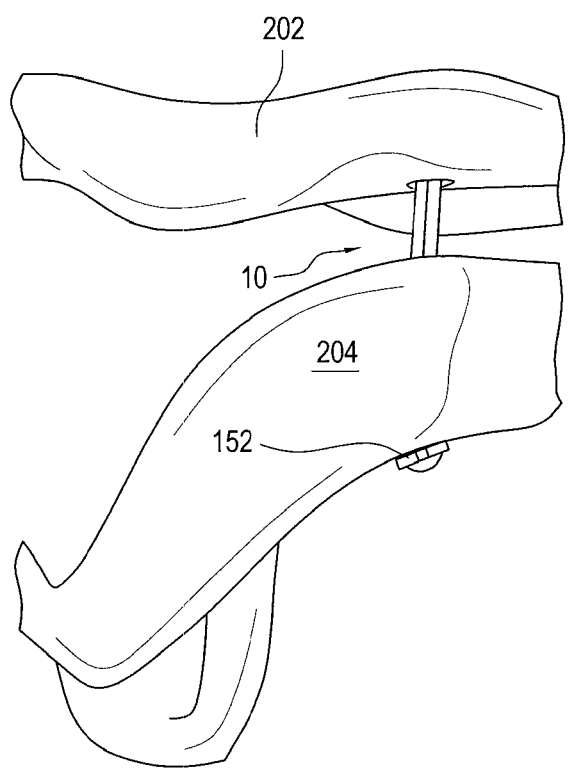
Figure 6G:
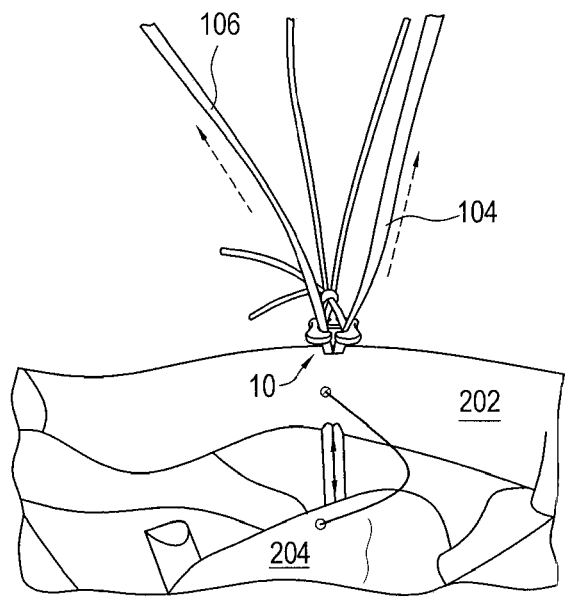

Once the fixation device 152 is attached to the adjustable loops 108 and 110 of the construct 10, the free ends 104 and 106 may be pulled in a second direction from the coracoid 204 to the clavicle 202 so that the fixation device 152 engages the coracoid 204, that is it abuts a superior surface of the coracoid, as seen in FIGS. 6E and 6F. Continued pulling of the construct in this direction closes the separation S between the clavicle 202 and the coracoid 204, as seen in FIGS. 6F and 6G, thereby stabilizing the dislocation.

Figure 6H:
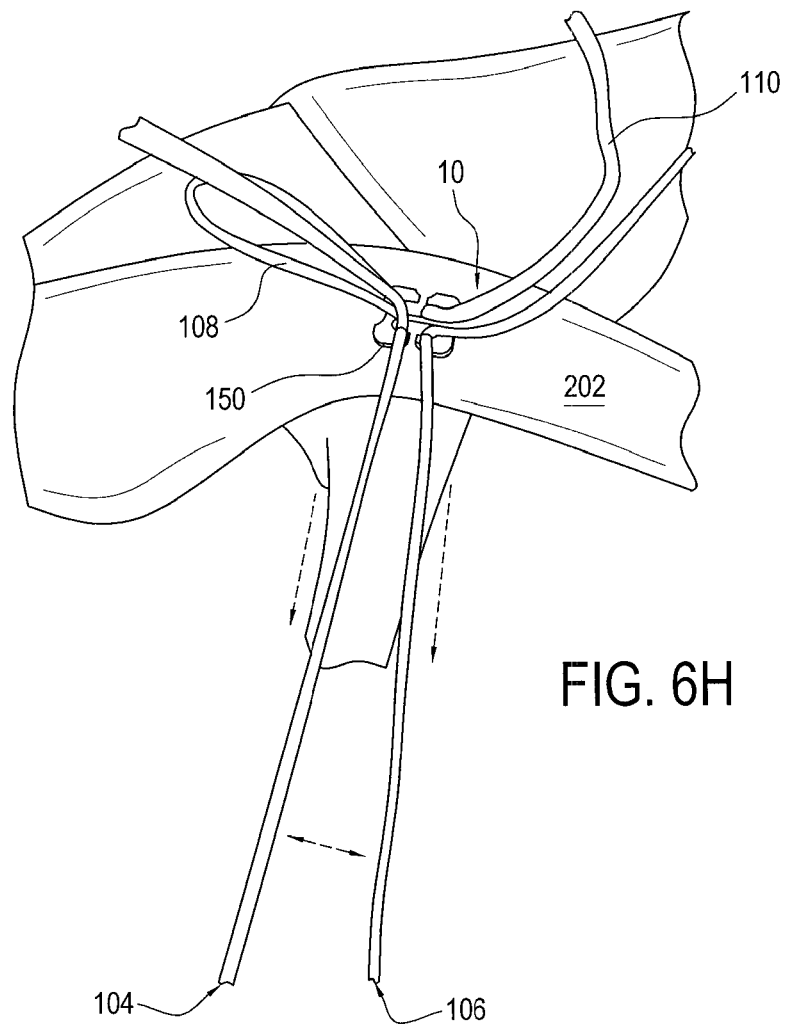
Figure 6I:
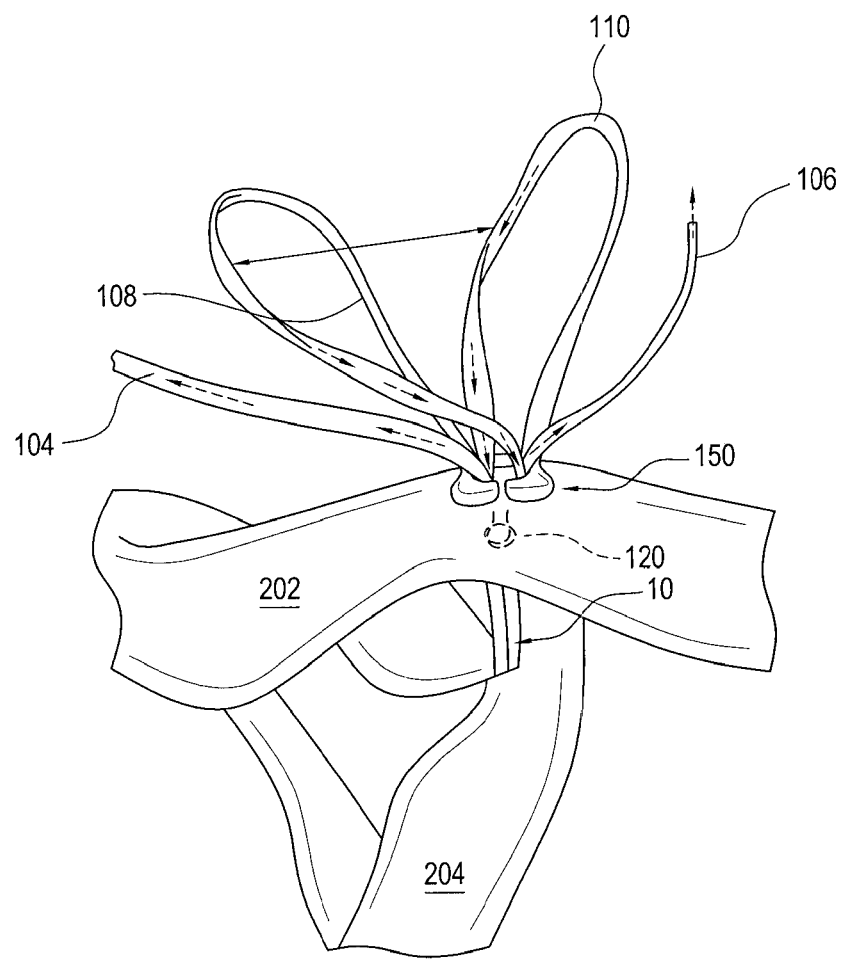
Figure 6J:
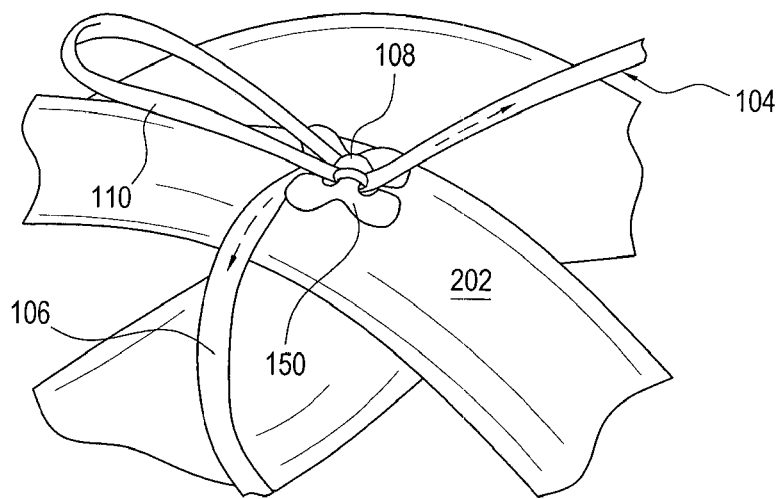
Figure 6K:
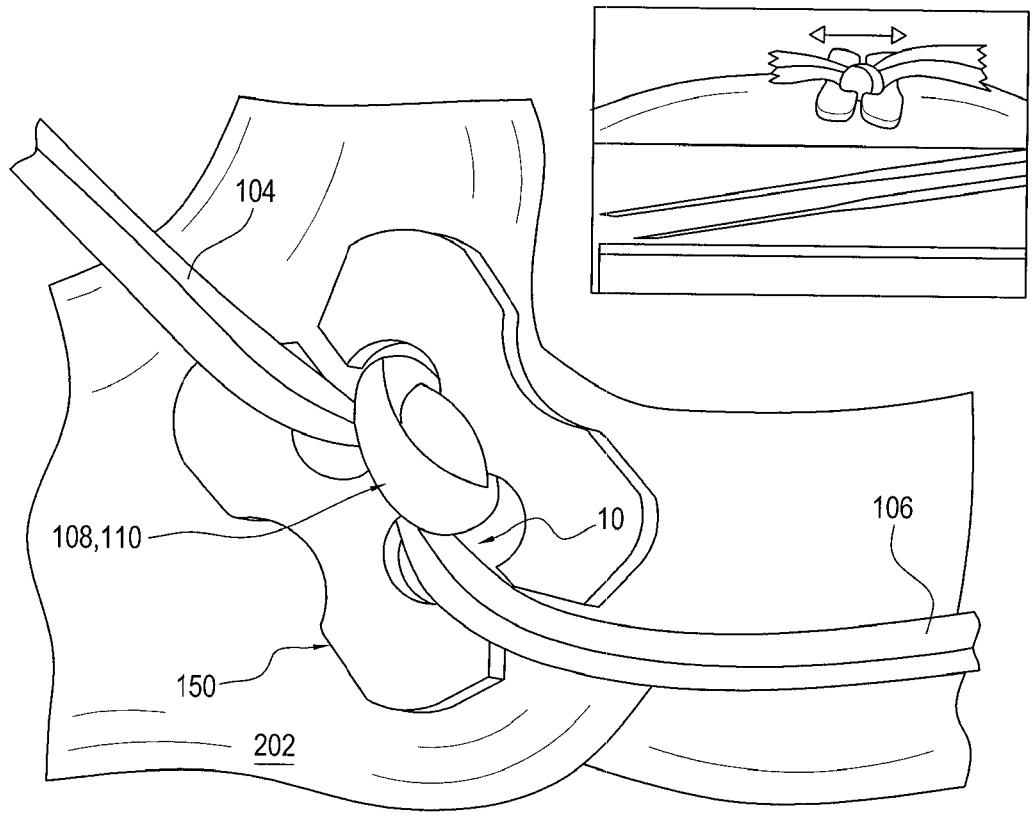
Figure 6L:
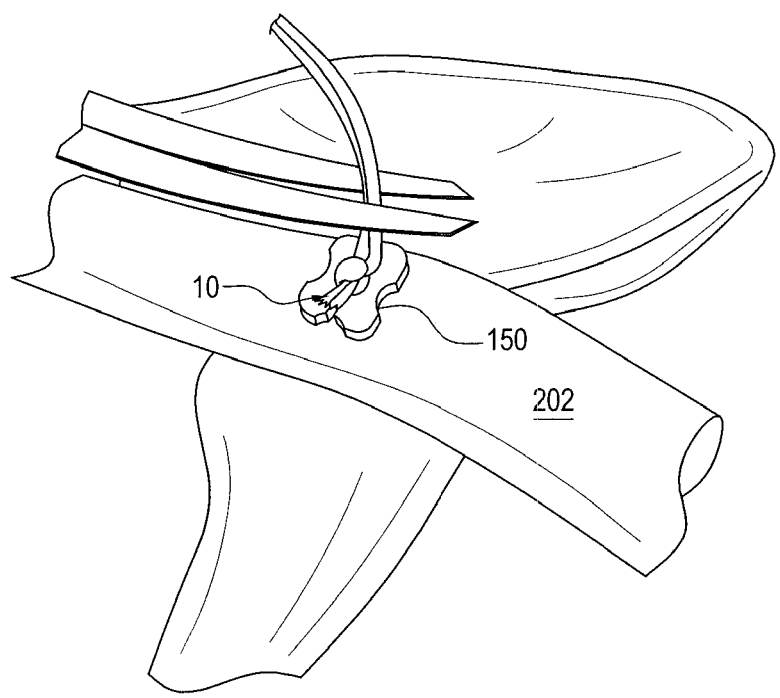

The flexible strand of the construct 10 may then be pulled, by using a wire or other shuttling device, through the sliding knot 120 in clavicle 202 and through fixation device 150, as seen in FIG. 6H. The fixation device 150 may be advanced to engage the clavicle 202, that is it abuts a superior surface of the clavicle. The adjustable loops 108 and 110 are now ready to be closed to secure the repair by tensioning the free ends 104 and 106 and sliding the same through sliding knot 120, as seen in FIG. 6I, with little to no friction. As seen in FIG. 6J, the adjustable loops 108 and 110 may be tightened one at a time by pulling one of the free ends 104 and 106 and then the other. Alternatively, the adjustable loops 108 and 110 may be tightened at the same time but pulling the free ends 104 and 106 at the same time. Once the loops are completely tightened against the fixation device 150, the free ends 104 and 106 may be cut, as seen in FIGS. 6K and 6L. The fixation device being attached with the adjustable loops and sliding knot of the construct 10, provides a better fixation without requiring numerous knots, and without needed to use two separate sutures or fiber tapes. Using a single flexible strand, such as a suture tape, doubles the strength of the fixation because the single tape passes twice through the button.

A CCL reconstruction using the construct 10 provides a minimally invasive method for extracapsular stabilization of the cranial cruciate ligament deficient canine stifle. For a CCL reconstruction, the construct 10 may be configured to optimize the lateral suture stabilization technique by employing bone-to-bone fixation, an implant with superior strength and stiffness, that may be designed specifically for ligament repair, and a method for consistent isometric implant placement. As such, CCL reconstruction using the construct 10 can counteract cranial tibial thrust, drawer, and internal rotation while providing optimal joint range-of-motion. With the adjustable loop and sliding knot allows the use of only one suture or suture tape with the sliding knot construct 10 resulting in a low profile knot for the final fixation.

Figure 7:
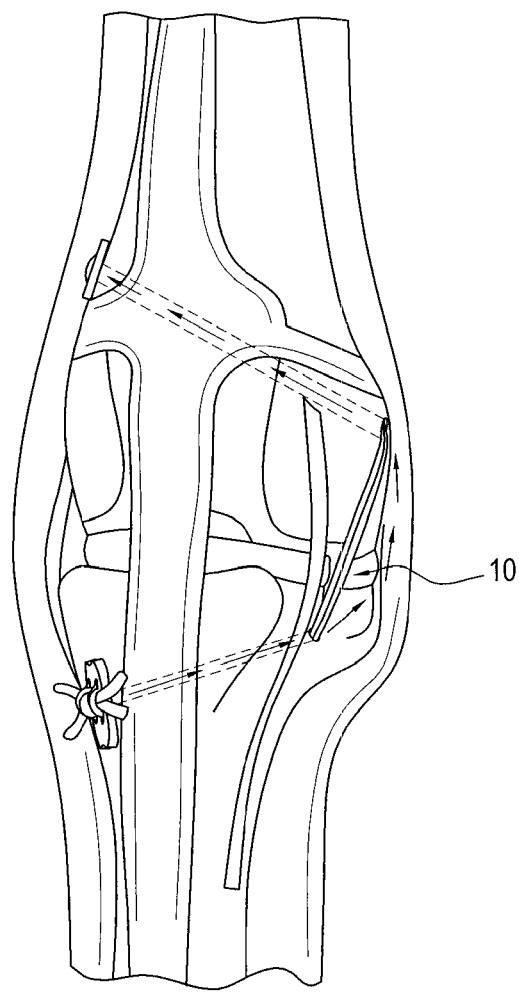
FIG. 7 shows the final fixation of a CCL reconstruction using the surgical construct illustrated in FIGS. 1A and 1B.

For the CCL reconstruction, the bones, i.e. the femur and the tibia, are prepared in a similar manner as above and the construct 10 is similarly passed through the tibia and then through the femur, via a shuttle device such as a wire. The wire may have a fiber wire loop attached to a button implant. The button may be placed on the femur and another button may be mounted on the end of the tibia. At this point, the CCL reconstruction is similar to the AC joint reconstruction described above, except that the button that is coupled to the construct goes on the tibia at the final fixation. The button is already attached with the adjustable loops and sliding knot of the construct 10, thereby providing a better fixation without doing numerous knots, and without needed to use two separate sutures or fiber tapes, as seen in FIG. 7. Using a single flexible strand, such as a suture tape, doubles the strength of the fixation because the single tape passes twice through the button.

Although use of the surgical construct 10 is described in connection with a joint separation or CCL reconstruction, surgical construct 10 may be used for other tissue repairs, including soft tissue-to-bone repairs. The surgical construct 10 may also be used with only one of the fixation devices or no fixation devices depending on the type of repair or reconstruction.

It should be understood that terms such as "lateral," "medial," "distal," "proximal," "superior," and "inferior" are used above consistent with the way those terms are used in the art. Further, these terms have been used herein for purposes of explanation and should not be considered otherwise limiting. Terms such as "generally," "substantially," and "about" are not intended to be boundary less terms and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

What is claimed is:

1. A surgical construct, comprising:
   a flexible strand comprising,
      a first segment, a second segment, and opposite first and second free ends corresponding to the first and second segments, respectively, the first segment forming a first adjustable loop and the second segment forming a second adjustable loop, each of the first and second adjustable loops having a continuous loop portion, the continuous loop portions being interlocked with one another, and
      a sliding knot coupling the first and second segments, the sliding knot being configured to slidably receive the first and second free ends,
      wherein the continuous loop portions of the first and second adjustable loops are interconnected across from the sliding knot and the continuous loop portions terminate at the sliding knot,
      wherein the first and second adjustable loops are individually adjustable independent of one another by sliding the first and second free ends through the sliding knot, and
      wherein the flexible strand is devoid of splicing.

2. The surgical construct of claim 1, wherein the flexible strand is a single flexible strand.

3. The surgical construct of claim 1, wherein the flexible strand is a suture or a suture tape.

4. The surgical construct of claim 1, wherein a fixation device is coupled to the first and second free ends of the flexible strand.

5. The surgical construct of the claim 4, wherein the fixation device is located near the sliding knot.

6. The surgical construct of claim 4, wherein the fixation device is a button that has apertures for receiving each of the first and second adjustable loops.

7. A surgical construct for tissue reconstruction, comprising:
   a single suture tape comprising,
      a first segment, a second segment, and opposite first and second free ends corresponding to the first and second segments, respectively, the first segment forming a first adjustable loop and the second segment forming a second adjustable loop, each of the first and second adjustable loops having a continuous loop portion, and
      a sliding knot coupling the first and second segments and terminating the continuous loop portions, the sliding knot being configured to slidably receive the first and second free ends,
      wherein the first and second adjustable loops are individually adjustable independent of one another by sliding the first and second free ends through the sliding knot.

8. The surgical construct of claim 7, wherein the continuous loop portions of the first and second adjustable loops are interconnected.

9. The surgical construct of claim 8, wherein the continuous loop portions are interconnected across from the sliding knot.

10. The surgical construct of claim 7, wherein a fixation device is coupled to the first and second free ends of the flexible strand.

11. The surgical construct of claim 10, wherein the fixation device is a button.

12. The surgical construct of claim 7, wherein the flexible strand is devoid of splicing.

13. A method of tissue reconstruction, comprising the steps of:
    advancing a surgical construct in a first direction through first and second tissues, the surgical construct being formed of a flexible strand comprising first and second interlocked adjustable loops, a sliding knot, and first and second free ends slidable through the sliding knot;
    pulling the surgical construct in a second direction opposite the first direction at the first and second free ends thereof such that a fixation device coupled to the first and second adjustable loops engages the first tissue and closing a separation between the first and second tissues; and
    tensioning the surgical construct by pulling on the free ends to reduce the first and second adjustable loops and secure the first and second tissues together.

14. The method of claim 13, further comprising the steps of engaging another fixation device coupled to the free ends of the surgical construct with the second tissue, wherein tensioning the surgical construct by pulling on the free ends to reduce the first and second adjustable loops, secures the first and second tissues together between the fixation devices.

15. The method of claim 14, wherein the another fixation device is coupled to the free ends of the surgical construct prior to inserting the surgical construct through the first and second bones.

16. The method of claim 14, wherein each of the fixation devices is a button.

17. The method of claim 13, wherein the first and second adjustable loops are individually adjustable by pulling the first and second free ends, respectively, when tensioning the surgical construct.

18. The method of claim 13, wherein the first and second adjustable loops are simultaneously adjustable by pulling on the first and second free ends at the same time.

19. The method of claim 14, wherein the first and second tissues are first and second bones of a separated bone joint.

20. The method of claim 19, wherein corresponding holes are drilled into the first and second bones and the surgical construct is advanced through the holes of the first and second bones.

21. The method of claim 20, wherein the sliding knot of the surgical construct is placed in the hole of the second bone.

22. The method of claim 19, wherein when the surgical construct is advanced through the first and second bones, the adjustable loops of the surgical construct are first inserted into the holes of the first and second bones, respectively.

23. The method of claim 13, wherein the fixation device is coupled to the adjustable loops of the surgical construct after the step of advancing the surgical construct through the first and second bones.

24. The method of claim 13, wherein the flexible strand is a single suture tape.

25. The method of claim 13, wherein the flexible strand is devoid of splicing.

26. A surgical construct, comprising:
a flexible strand comprising,
   a first segment, a second segment, and opposite first and second free ends corresponding to the first and second segments, respectively, the first segment forming a first adjustable loop and the second segment forming a second adjustable loop, each of the first and second adjustable loops having a continuous loop portion, the continuous loop portions being interlocked with one another, and
   a sliding knot coupling the first and second segments, the sliding knot being configured to slidably receive the first and second free ends,
   wherein the continuous loop portions of the first and second adjustable loops are interconnected across from the sliding knot and the continuous loop portions terminate at the sliding knot, and
   wherein the first and second adjustable loops are individually adjustable independent of one another by sliding the first and second free ends through the sliding knot.

27. A surgical construct, comprising:
a flexible strand comprising,
   a first segment, a second segment, and opposite first and second free ends corresponding to the first and second segments, respectively, the first segment forming a first adjustable loop and the second segment forming a second adjustable loop, each of the first and second adjustable loops having a continuous loop portion, the continuous loop portions being interlocked with one another, and
   a sliding knot coupling the first and second segments, the sliding knot being configured to slidably receive the first and second free ends,
   wherein the first and second adjustable loops are individually adjustable independent of one another by sliding the first and second free ends through the sliding knot, and
   wherein a fixation device is coupled to the first and second free ends of the flexible strand.

28. A surgical construct, comprising:
a flexible strand comprising,
   a first segment, a second segment, and opposite first and second free ends corresponding to the first and second segments, respectively, the first segment forming a first adjustable loop and the second segment forming a second adjustable loop, each of the first and second adjustable loops having a continuous loop portion, the continuous loop portions being interlocked with one another, and
   a sliding knot coupling the first and second segments, the sliding knot being configured to slidably receive the first and second free ends,
   wherein the first and second adjustable loops are individually adjustable independent of one another by sliding the first and second free ends through the sliding knot, and
   wherein the flexible strand is devoid of splicing; and
a fixation device coupled to the first and second free ends of the flexible strand.

* * * * *